(12) United States Patent
Lan et al.

(10) Patent No.: US 6,740,517 B2
(45) Date of Patent: May 25, 2004

(54) INCUBATION METHOD FOR OBTAINING SOLID CULTURE OF ZANG ZHI, SOLID CULTURE OBTAINED THEREFROM, PROCESSED PRODUCTS AND USE THEREOF

(76) Inventors: Ming-Huang Lan, 7F, No. 9, Lane 191, Sec. 2, Di-Hua St., Taipei (TW); Li-Yu Wu, 7F, No. 9, Lane 191, Sec. 2, Di-Hua St., Taipei (TW)

( * ) Notice: Subject to any disclaimer, the term of this patent is extended or adjusted under 35 U.S.C. 154(b) by 0 days.

(21) Appl. No.: 10/023,362

(22) Filed: Dec. 14, 2001

(65) Prior Publication Data

US 2003/0138408 A1 Jul. 24, 2003

(51) Int. Cl.$^7$ .......................... C12N 1/14; A01N 63/04; A01N 35/84; A61K 35/84
(52) U.S. Cl. ...................... 435/254.3; 435/41; 435/915; 424/93.15; 424/195.15; 424/520; 424/780
(58) Field of Search .......................... 424/93.5, 195.15, 424/520, 780; 435/41, 254.3, 915

(56) References Cited

PUBLICATIONS

Yang, S.W. et al. 1986. Phytochemistry, 41: 1389–1392.*
Wu et al. Bot. Bull. Acad. Sin. 1997, vol. 38, pp. 273–275.*
Endrawanto, S.E. Abstract, Proceeding of the Scientific Meeting of Research and Development of Isotope and Radiation Technology, 2000, pp. 169–173.*
Zhang, J. et al. Biosci., Biotech. Biochem. 1994. 58:1202–1205.*
Wang, Zu–Nan, Studies on Ganoderma, Lentinus and Auricularia Fungi, Taiwan Sugar Research Institute, No. 130, Dec. 1990, 10 pages.

* cited by examiner

Primary Examiner—Christopher R. Tate
Assistant Examiner—Kailash C. Srivastava
(74) Attorney, Agent, or Firm—Ladas & Parry (57) ABSTRACT

A solid culture of Zang Zhi (*Antrodia camphorata*) having triterpenoid compounds, water-soluble polysaccharides and chitin. The solid culture is prepared by a method including the steps of: incubating a stock strain of Zang Zhi in a bag for growth of mycelia, followed by an incubation in the air for fruiting the Zang Zhi body.

4 Claims, 7 Drawing Sheets

INCUBATION METHOD FOR OBTAINING SOLID CULTURE OF ZANG ZHI, SOLID CULTURE OBTAINED THEREFROM, PROCESSED PRODUCTS AND USE THEREOF

BACKGROUND OF THE INVENTION

Zang Zhi is a kind of fungus. Its academic name is *Antrodia camphorata*, also known as "Zang ku", "red Zang Zhi", "niou Zang Zhi" or "niou Zang ku." In Taiwan, Zang Zhi only grows on the inner wall of the empty rotting trunk of *Cinnamomum kanehirai* in the shape of a platy or bell and has a strong cinnamon flavor. People say that Zang Zhi can tranquilize, prevent or treat a cold, promote vital energy circulation, remove blood stasis, promote blood circulation, relieve dyspepsia, detoxify and promote the subsidence of swelling, calm the nerves to reduce stress, alleviate pain, and is the best anticorrosive and detoxicant. It is considered the most expensive wild fungus in the market on Taiwan. The mechanism of anti-tumor cells of Zang Zhi is different from that of Ganoderma sp., which indirectly promotes immunity against tumors. Zang Zhi can directly inhibit or kill cancer cells, and has the capacity to strengthen the heart, adjust immunity, and antagonize the parasympathetic nervous system, and has serous activity. In particular, Zang Zhi can cure a stomachache, bowelache, nausea, diabetes, gout, arthritis, fever, allergy, exorbitant urine proteins, uremia, cirrhosis, hepatomia, flu, etc. Many research institutions have invested human resources and materials in the study of the active constituents of Zang Zhi. Among them, the National Science Council of the Executive Yuan has a special research project to make use of chemical methods, NMR spectrum analysis, and comparative spectrum with known materials to establish the constitutive characteristics of active constituents. Research results of the active constituents show that the water and methanol extracts of Zang Zhi are effective on the inhibition of the growth of *Streptococcus aureus* and *Trichophytone mentagrophytes*. Zhankuic acid A, a methanol extract of Zang Zhi has conspicuous inhibition to the lymphoma cells of a p-388 mouse and agglutination of blood platelets. Zhankuic acid B, however, shows little anticholinergic and anti-serotonin effect.

It is indicated in Gau Sheau Jy's masters thesis on the triterpenoid of Zang Zhi that Zang Zhi is a new species of Ganoderma discovered in 1990. The extract of the solid fruiting body is obtained by use of acetone, and then is separated and re-crystallized with chromatography LC and PLC. The purity of the extract is identified by TLC scanning and HPLC. The configuration test is done with mass spectrum, infrared spectrum, ultraviolet spectrum, H-NMR, and C-NMR. 3,11-dioxo-8,23-dien-26-oic acid can reduce GPT in the blood of a mouse with the acute hepatitis induced by $CCl_4$.

Most of Zang Zhi grows in the broad-leaf forest areas in Taiwan's East Coast Mountain Range. However, according to the bulletin of the Niou Zang Conservation Notice issued by the Taiwan Forestry Bureau, this mountain range has been listed as a natural resources conservation zone. Since Zang Zhi is a very popular product which most people are willing to purchase in Asia, Zang Zhi growing outside the said zone have been almost completely harvested. In fact, wild Zang Zhi is not available in the local markets.

With an estimated sale of 500 kg Zang Zhi per month in Taiwan, the requirement to provide an incubation method for solid culture of Zang Zhi has become more important in recent years.

SUMMARY OF THE INVENTION

The main objective of the subject invention is to provide an incubation method for solid culture of Zang Zhi. The cultured Zang Zhi will have the same pharmaceutical efficacy as wild Zang Zhi has.

The other objective of this invention is to provide a solid culture of Zang Zhi by use of the inoculums of Zang Zhi spawn preserved in the Food Industry Research and Development Institute (Taiwan), coded CCRC 35398, to incubate the solid culture in accordance with the incubation method.

Another objective of the invention is to provide the processed products of the solid cultured Zang Zhi.

Another objective of the invention is to provide a solid cultured Zang Zhi useful as active constituents.

DETAILED DESCRIPTION OF THE INVENTION

This invention provides a method for the solid culture of Zang Zhi, in order to produce a Zang Zhi fruiting body with the constituents and vatality of wild Zang Zhi. The invention's method for the solid culture of Zang Zhi is to culture the spawn of Zang Zhi through "Bag Log" cultivation, and then to produce the fruiting body of Zang Zhi in the air.

Before the phase of mycelium culture, one can greatly multiply the spawn for "Bag Log" cultivation, including the following three steps: (1) taking a piece of medium agar containing hyphae preserved in liquid nitrogen, and transferring it into a fresh medium to culture under constant temperature until the exuberant growth of mycelium appears; (2) inoculating the spawn into the "Bag Log" containing cellulolytic substance (for example kernel or spelk); (3) removing the old hyphae until the hyphae overgrows in the "Bag Log"; and (4) then inoculating the multiplied spawn into "Bag Log".

Before the phase of mycelium culture, one also can greatly multiply spawn with the liquid culture fermentation, and then inoculate them into "Bag Log". The formulation of liquid culture fermentation is 1–3% of fructose, 0.01–0.1% of magnesium sulfate, 0.1–1% of yeast extract, and 0.05–0.5% of potassium phosphate. The best formulation of liquid culture fermentation followed was 2% of fructose, 0.05% of magnesium sulfate, 0.5% of yeast extract, and 0.1% of potassium phosphate.

After culturing the slide tube, one may inoculate the multiplied spawn into a 5 liter liquid culture for fermentation under 24–26° C., 240 rpm oscillation for 14 days, and then 90 rpm oscillation for 14 days, and then inoculate them into a 20 liter liquid fermentation, stirring culture for 14 days.

Here, the so-called "Bag Log" is a plastic bag containing a sawdust medium made from 10–70% of cellulolytic material of stem, stalk, fruit, or spelk of any mushroom or plant (preferably the stems, stalks and fruits of grass plants or cellulolytic spelk) 10–30% of starch resource (preferably potato), and 5–15% of millet (preferably rice bran), 1–10% of saccharides (preferably glucose), 0.5% of phosphate (preferably potassium phosphate), and 0.1–1% of sulfate salt (preferably magnesium sulfate). Relative humidity is maintained at 60–90%, preferably at 80%. The pH value of the culture medium is adjusted to be neutral.

The phase of mycelium culture indicated in this text means a period of sixty days after the spawn is inoculated into "Bag Log". Mycelium will grow at a temperature from 5° to 32° C.; in particular, 28° C. is the best temperature for the growth of mycelium. "Bag Log" cultivation is under way at a relative humidity of about 60–80% and preferably at about 80%. As to the condition of air, 0.1–1% of carbon dioxide is preferable for the culture.

After the phase of mycelium culture, the phase of the culture of the fruiting body is next. That is to say 61–90 days after the date of the inoculation of the spawn, the plastic bag of "Bag Log" is to be removed, to let the sawdust medium be completely exposed to the air. During the phase of the culture of the fruiting body, the difference between day and night temperature has to be under strict control. Day temperature is generally maintained between 20° and 30° C., especially, better at 25±1° C.; night temperature is better maintained at 11±1° C.; the difference between day and night temperature is better maintained at 15° C. The relative humidity at the phase of fruiting body culture is controlled between 90 and 95%. In addition, the fruiting body has to be cultured in the moving air, and the carbon dioxide is less than 1%. Generally, solid culture material will be collected after 90–120 days.

The strain CCRC35398 spawn used in this invention can be obtained from the Food Industry Research and Development Institute, Taiwan. According to the solid culture method of this invention, a solid culture substance was obtained. The solid culture substance is conoid, about 10–30 cm in diameter, 15–30 cm in height, and 0.2–0.6 kg in weight.

To use the solid culture method described above, one can get the solid Zang Zhi. The solid Zang Zhi can be produced by any of the processing methods known to those skilled in the art, for example, water or alcohol can be used to extract the active constituents, and then known concentration methods such as vacuum concentration or freeze concentration can be used to produce the concentrated product.

One can use the dehydrated method to do the dehydration, or by a spray-dry or lyophilization method. However, the lyophilization method is the best one to dehydrate the solid substance, and during dehydration the solid substance will not change its characteristic by the effect of oxygen.

The microscopic particles produced by the spray-dry or other dehydration method can be agglomerated to increase their diameters. These products are poremeric particles with good wettability.

Figure 1:
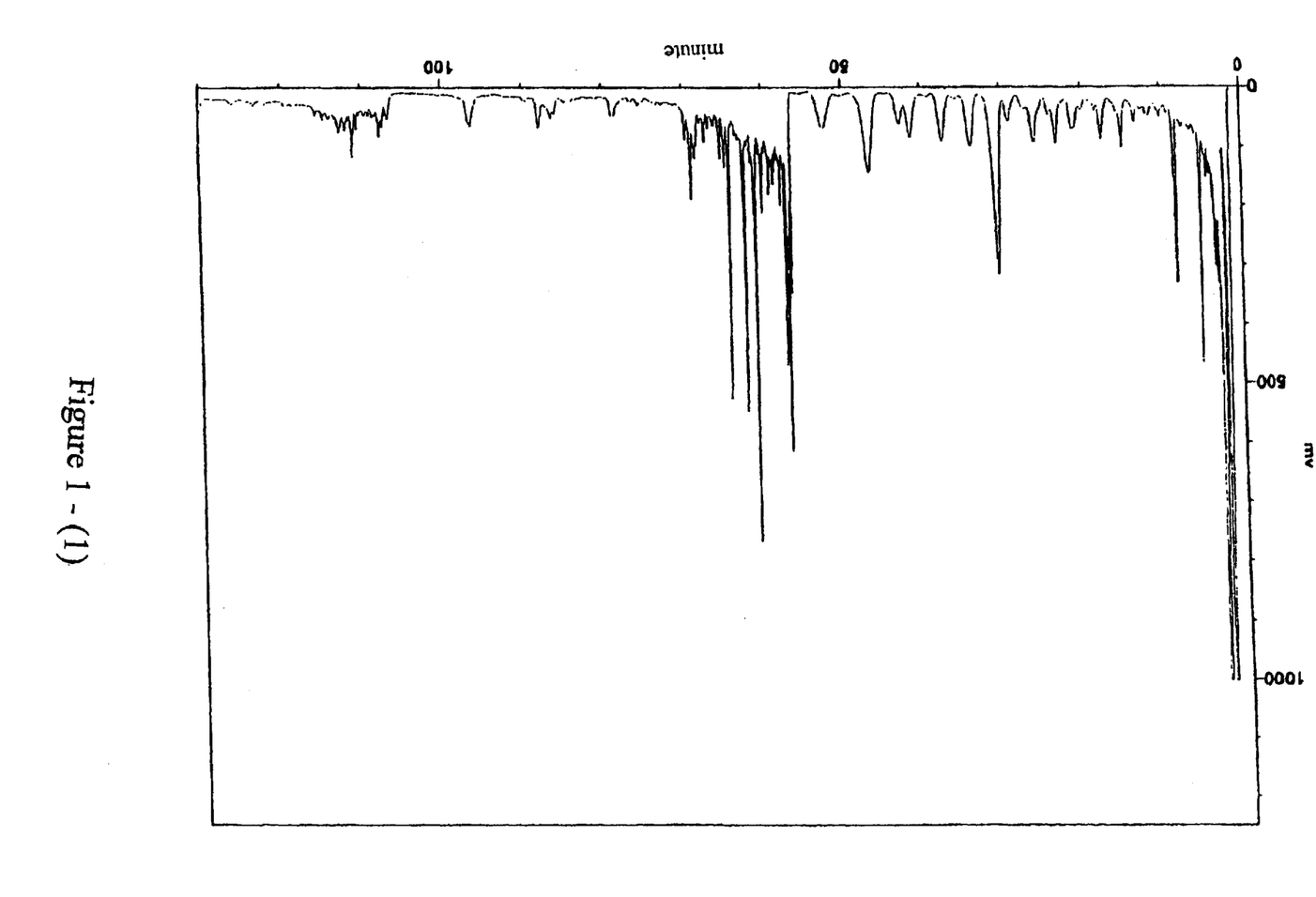
FIGS. 1a–c illustrate comparative analysis of the HPLC of constituents of Zang Zhi, including (a) the fruiting body of cultured Zang Zhi according to the invention, (b) the liquid culture of Zang Zhi and (c) the fruiting body of wild Zang Zhi.

The comparative HPLC spectrum of the invention's solid culture Zang Zhi, known liquid cultured Zang Zhi, and wild Zang Zhi is shown in FIG. 1. By analysis of HPLC, the constituents of the fruiting body obtained through the invention's culture method are similar to those of the wild Zang Zhi and the invention's Zang Zhi has the activities and functions similar to the wild Zang Zhi's. These activities and functions include tranquilization, prevention from or treatment of a cold, promoting vital energy circulation, removing blood stasis, promoting blood circulation, relieving dyspepsia, detoxifying and promoting the subsidence of swelling, calming the nerves to reduce stress, alleviating pain, inhibiting bacteria and virus and cancer cells, strengthening the heart, adjusting immunity, and antagonizing the parasympathetic nervous system and serous activity. Zang Zhi can cure a stomachache and bowel ache, nausea, diabetes, gout, arthritis, infection, allergy, exorbitant urine proteins, uremia, cirrhosis, hepatomia, flu and so on. Zang Zhi can regenerate skin and act as human skin or callus material, or as adhesive for bedsore or traumatic skin.

Furthermore, the invention's solid cultured substance possesses the abilities to antagonize the free radicals and peroxidation of lipids, and functions to protect the liver and inhibit cancer cells. The invention's solid cultured substance can be taken as health food to prolong life, and be further developed into new medicines.

The following working examples will further explain this invention, but not limit this invention. Any application or modification of this invention made by persons skilled in these techniques will fall in the scope of this invention.

WORKING EXAMPLES

The strain CCRC3598 spawn obtained from the Food Industry Research and Development Institute were grown by ferment liquid culture, and then inoculated into the "Bag Log". The fermented liquid culture contains 2% of fructose, 0.5% of magnesium sulfate, 0.5% of yeast extract, and 0.1% of potassium phosphate. "Bag Log" cultivation is to culture mycelium. "Bag Log" is composed of 65% of the stems, stalks, fruits of grass plants or cellulolytic spelk, 20% of potato, 10% of rice bran, 3.5% of glucose, 1% of potassium phosphate, and 0.5% of magnesium sulfate. Adjust the relative humidity to 80% and pH to 7. Relative humidity was maintained at 60–90% preferably at 80%, and the pH of the culture medium was adjusted to being neutral.

The period of mycelium culture is 60 days after the spawn was inoculated into "Bag Log". Mycelium will grow at a temperature between 5° and 32° C.; 28° C. is the optimal temperature for the growth of mycelium. "Bag Log" humidity is at 80%, and air condition is 0.2–1% of carbon dioxide.

After the phase of the mycelium culture, the phase of the culture of the fruiting body is done, that is to say 61–90 days after the date of inoculation of the spawn, the plastic bag of "Bag Log" is to be removed, to let the sawdust medium be completely exposed in the air. During the phase of the culture of the fruiting body, the difference between day and night temperature has to be under strict control. Day temperature is generally maintained between 20° and 30° C.; night temperature is better maintained at 11±1° C.; the difference between day and night temperature is better maintained at 15° EC. The relative humidity of the phase of the fruiting body culture is controlled between 90 and 95%. In addition, the fruiting body has to be cultured in the moving air, and the carbon dioxide is less than 1%.

In 90–120 days, when the conoid fruiting body grows up to 15 cm in diameter and 25 cm in height, the solid-cultured substance will be collected, and then the substance is about 0.4 kg in weight. The HPLC spectrum of major active elemetns—triterpenoid—is shown FIG. 1(a), and the measurements are shown in the following Table 1.

Table 1, Data of HPLC Analysis of the Invention's Zang Zhi Fruiting Body

TABLE 1

| No. | retention time | area (uv*sec) | area % | relative height | height % | conc | conc unit | basline | ingredient name |
|---|---|---|---|---|---|---|---|---|---|
| 1 | 2.060 | 27958870 | 9.3018 | 1000.279 | 6.5362 | 0.0000 | | PV | |
| 2 | 2.547 | 6320387 | 2.1028 | 999.303 | 6.5299 | 0.0000 | | VV | |
| 3 | 2.663 | 6333234 | 2.1070 | 999.158 | 6.5289 | 0.0000 | | VV | |
| 4 | 2.823 | 13521140 | 4.4984 | 998.886 | 6.5271 | 0.0000 | | VV | |
| 5 | 3.117 | 3933511 | 1.3087 | 328.263 | 2.1450 | 0.0000 | | VV | |
| 6 | 3.413 | 4614312 | 1.5352 | 303.141 | 1.9808 | 0.0000 | | VV | |
| 7 | 3.673 | 2519874 | 0.6364 | 182.128 | 1.1901 | 0.0000 | | VV | |
| 8 | 3.973 | 2084553 | 0.6935 | 144.477 | 0.9441 | 0.0000 | | VV | |
| 9 | 4.367 | 4265658 | 1.4192 | 149.458 | 0.9766 | 0.0000 | | VV | |
| 10 | 5.150 | 7601131 | 2.5289 | 460.320 | 3.0079 | 0.0000 | | VV | |
| 11 | 5.773 | 1671478 | 0.5561 | 71.272 | 0.4657 | 0.0000 | | VB | |
| 12 | 6.043 | 441685 | 0.1469 | 54.184 | 0.3541 | 0.0000 | | BV | |
| 13 | 6.360 | 1264481 | 0.4207 | 62.749 | 0.4100 | 0.0000 | | VV | |
| 14 | 6.597 | 1359149 | 0.4522 | 58.680 | 0.3834 | 0.0000 | | VV | |
| 15 | 7.263 | 1946283 | 0.6475 | 56.407 | 0.3686 | 0.0000 | | VV | |
| 16 | 7.660 | 517391 | 0.1721 | 43.081 | 0.2815 | 0.0000 | | VV | |
| 17 | 8.167 | 5862269 | 1.9504 | 317.837 | 2.0769 | 0.0000 | | VV | |
| 18 | 8.983 | 932610 | 0.3103 | 29.915 | 0.1955 | 0.0000 | | VV | |
| 19 | 9.990 | 1253931 | 0.4172 | 34.691 | 0.2267 | 0.0000 | | VV | |
| 20 | 10.343 | 538013 | 0.1790 | 22.899 | 0.1496 | 0.0000 | | VV | |
| 21 | 10.823 | 164318 | 0.0547 | 12.337 | 0.0806 | 0.0000 | | VV | |
| 22 | 11.327 | 1233415 | 0.4104 | 29.716 | 0.1942 | 0.0000 | | VV | |
| 23 | 12.193 | 628302 | 0.2090 | 19.258 | 0.1258 | 0.0000 | | VV | |
| 24 | 12.990 | 1259055 | 0.4189 | 37.378 | 0.2442 | 0.0000 | | VP | |
| 25 | 14.810 | 2982581 | 0.9923 | 80.403 | 0.5254 | 0.0000 | | PP | |
| 26 | 17.313 | 2521967 | 0.8390 | 68.342 | 0.4466 | 0.0000 | | PV | |
| 27 | 18.113 | 627346 | 0.2087 | 19.934 | 0.1303 | 0.0000 | | VV | |
| 28 | 18.990 | 117339 | 0.0390 | 4.690 | 0.0306 | 0.0000 | | VV | |
| 29 | 19.867 | 663514 | 0.2207 | 20.198 | 0.1320 | 0.0000 | | VV | |
| 30 | 20.867 | 2932057 | 0.9755 | 52.760 | 0.3448 | 0.0000 | | VV | |
| 31 | 22.323 | 252149 | 0.0839 | 9.636 | 0.0630 | 0.0000 | | VV | |
| 32 | 23.080 | 3131662 | 1.0419 | 79.476 | 0.5193 | 0.0000 | | VV | |
| 33 | 23.960 | 1130832 | 0.3762 | 31.023 | 0.2027 | 0.0000 | | VV | |
| 34 | 25.857 | 4135840 | 1.3760 | 78.025 | 0.5098 | 0.0000 | | VV | |
| 35 | 26.910 | 1070268 | 0.3561 | 22.420 | 0.1465 | 0.0000 | | VP | |
| 36 | 28.940 | 2127664 | 0.7079 | 44.217 | 0.2889 | 0.0000 | | PV | |
| 37 | 30.503 | 15997700 | 5.3224 | 304.306 | 1.9885 | 0.0000 | | VP | |
| 38 | 33.793 | 5256445 | 1.7488 | 92.365 | 0.6036 | 0.0000 | | PV | |
| 39 | 35.573 | 462920 | 0.1540 | 8.405 | 0.0649 | 0.0000 | | VV | |
| 40 | 37.360 | 4416830 | 1.4695 | 79.089 | 0.5168 | 0.0000 | | VP | |
| 41 | 39.193 | 261669 | 0.0871 | 5.522 | 0.0361 | 0.0000 | | PV | |
| 42 | 41.267 | 4411946 | 1.4678 | 73.326 | 0.4791 | 0.0000 | | VV | |
| 43 | 42.667 | 2821209 | 0.9386 | 50.936 | 0.3328 | 0.0000 | | VV | |
| 44 | 44.323 | 36608 | 0.0122 | 1.071 | 0.0070 | 0.0000 | | VP | |
| 45 | 46.630 | 10087950 | 3.3562 | 134.950 | 0.8818 | 0.0000 | | PP | |
| 46 | 50.090 | 333401 | 0.1109 | 4.502 | 0.0294 | 0.0000 | | PV | |
| 47 | 52.383 | 4896649 | 1.6291 | 60.376 | 0.3945 | 0.0000 | | VP | |
| 48 | 55.280 | 124357 | 0.0414 | 2.047 | 0.0134 | 0.0000 | | PP | |
| 49 | 56.593 | 4986938 | 1.6591 | 340.488 | 2.2249 | 0.0000 | | PV | |
| 50 | 56.953 | 7314754 | 2.4336 | 625.513 | 4.0874 | 0.0000 | | VV | |
| 51 | 57.290 | 4586732 | 1.5260 | 463.198 | 3.0267 | 0.0000 | | VV | |
| 52 | 57.800 | 3699586 | 1.2308 | 189.756 | 1.2399 | 0.0000 | | VV | |
| 53 | 58.087 | 1056724 | 0.3516 | 118.120 | 0.7718 | 0.0000 | | VV | |
| 54 | 58.477 | 2468879 | 0.8214 | 134.218 | 0.8770 | 0.0000 | | VV | |
| 55 | 58.690 | 1982234 | 0.6595 | 157.526 | 1.0293 | 0.0000 | | VV | |
| 56 | 58.927 | 1445816 | 0.4810 | 124.837 | 0.8157 | 0.0000 | | VV | |
| 57 | 59.210 | 3138696 | 1.0442 | 171.327 | 1.1195 | 0.0000 | | VV | |
| 58 | 59.520 | 1098725 | 0.3655 | 89.794 | 0.5867 | 0.0000 | | VV | |
| 59 | 59.840 | 1481909 | 0.4930 | 102.506 | 0.6698 | 0.0000 | | VV | |
| 60 | 60.093 | 3406697 | 1.1334 | 202.433 | 1.3228 | 0.0000 | | VV | |
| 61 | 60.483 | 1645084 | 0.5473 | 104.449 | 0.6825 | 0.0000 | | VV | |
| 62 | 60.980 | 10587770 | 3.5225 | 757.281 | 4.9484 | 0.0000 | | VV | |
| 63 | 61.403 | 1626563 | 0.5412 | 117.086 | 0.7651 | 0.0000 | | VV | |

TABLE 1-continued

| No. | retention time | area (uv*sec) | area % | relative height | height % | conc | conc unit | basline | ingredient name |
|---|---|---|---|---|---|---|---|---|---|
| 64 | 61.700 | 856049 | 0.2848 | 79.162 | 0.5173 | 0.0000 | | VV | |
| 65 | 61.907 | 1498212 | 0.4984 | 88.354 | 0.5773 | 0.0000 | | VV | |
| 66 | 62.297 | 7358936 | 2.4483 | 538.464 | 3.5185 | 0.0000 | | VV | |
| 67 | 62.713 | 1007688 | 0.3353 | 76.731 | 0.5014 | 0.0000 | | PV | |
| 68 | 62.980 | 953127 | 0.3171 | 76.873 | 0.5023 | 0.0000 | | VV | |
| 69 | 63.187 | 1992004 | 0.6627 | 69.898 | 0.4567 | 0.0000 | | VV | |
| 70 | 63.803 | 776093 | 0.2582 | 55.283 | 0.3612 | 0.0000 | | VV | |
| 71 | 64.203 | 6164886 | 2.0510 | 515.260 | 3.3669 | 0.0000 | | VV | |
| 72 | 64.537 | 761873 | 0.2535 | 72.303 | 0.4725 | 0.0000 | | VV | |
| 73 | 64.773 | 2147592 | 0.7145 | 124.955 | 0.8165 | 0.0000 | | VV | |
| 74 | 65.287 | 2333203 | 0.7762 | 110.636 | 0.7229 | 0.0000 | | VV | |
| 75 | 65.987 | 1814540 | 0.6037 | 53.283 | 0.3482 | 0.0000 | | VV | |
| 76 | 66.627 | 1221936 | 0.4065 | 56.684 | 0.3704 | 0.0000 | | VV | |
| 77 | 67.103 | 1666644 | 0.5545 | 81.135 | 0.5302 | 0.0000 | | VV | |
| 78 | 67.617 | 1226534 | 0.4081 | 46.888 | 0.3064 | 0.0000 | | VV | |
| 79 | 68.340 | 3797130 | 1.2633 | 108.221 | 0.7072 | 0.0000 | | VV | |
| 80 | 68.910 | 3980780 | 1.3244 | 176.942 | 1.1562 | 0.0000 | | VV | |
| 81 | 69.637 | 2559917 | 0.8517 | 76.359 | 0.4990 | 0.0000 | | VV | |
| 82 | 70.970 | 680358 | 0.2264 | 16.357 | 0.1069 | 0.0000 | | VV | |
| 83 | 71.683 | 264668 | 0.0881 | 12.546 | 0.0820 | 0.0000 | | VV | |
| 84 | 72.387 | 686349 | 0.2283 | 14.902 | 0.0974 | 0.0000 | | VV | |
| 85 | 73.070 | 513554 | 0.1709 | 13.848 | 0.0905 | 0.0000 | | VV | |
| 86 | 73.730 | 419796 | 0.1397 | 9.953 | 0.0650 | 0.0000 | | VV | |
| 87 | 74.950 | 337733 | 0.1190 | 12.698 | 0.0830 | 0.0000 | | VV | |
| 88 | 75.373 | 465804 | 0.1550 | 15.474 | 0.1011 | 0.0000 | | VV | |
| 89 | 76.253 | 356155 | 0.1185 | 10.162 | 0.0664 | 0.0000 | | VV | |
| 90 | 77.137 | 133340 | 0.0444 | 4.645 | 0.0304 | 0.0000 | | VV | |
| 91 | 77.850 | 272953 | 0.0908 | 11.805 | 0.0771 | 0.0000 | | VV | |
| 92 | 78.420 | 752946 | 0.2505 | 30.824 | 0.2014 | 0.0000 | | VV | |
| 93 | 78.690 | 869866 | 0.2894 | 31.809 | 0.2079 | 0.0000 | | VV | |
| 94 | 79.653 | 66206 | 0.0220 | 2.235 | 0.0146 | 0.0000 | | VP | |
| 95 | 80.730 | 79648 | 0.0265 | 2.862 | 0.0187 | 0.0000 | | PP | |
| 96 | 81.753 | 27502 | 0.0091 | 1.070 | 0.0070 | 0.0000 | | PP | |
| 97 | 83.147 | 186611 | 0.0621 | 4.143 | 0.0271 | 0.0000 | | VV | |
| 98 | 83.923 | 293714 | 0.0977 | 9.081 | 0.0593 | 0.0000 | | VV | |
| 99 | 84.520 | 361025 | 0.1201 | 9.061 | 0.0592 | 0.0000 | | VV | |
| 100 | 85.820 | 820423 | 0.2730 | 29.144 | 0.1904 | 0.0000 | | VV | |
| 101 | 86.260 | 1531752 | 0.5096 | 35.708 | 0.2333 | 0.0000 | | VV | |
| 102 | 87.803 | 1945022 | 0.6471 | 51.978 | 0.3396 | 0.0000 | | VV | |
| 103 | 89.500 | 271109 | 0.0902 | 7.353 | 0.0480 | 0.0000 | | VP | |
| 104 | 90.883 | 26832 | 0.0089 | 0.533 | 0.0035 | 0.0000 | | PP | |
| 105 | 92.080 | 55385 | 0.0184 | 1.398 | 0.0091 | 0.0000 | | PP | |
| 106 | 96.443 | 3758662 | 1.2505 | 52.867 | 0.3455 | 0.0000 | | PP | |
| 107 | 100.237 | 94086 | 0.0313 | 1.137 | 0.0074 | 0.0000 | | PP | |
| 108 | 106.650 | 1435702 | 0.4777 | 41.107 | 0.2686 | 0.0000 | | PV | |
| 109 | 107.300 | 1158655 | 0.3855 | 55.895 | 0.3652 | 0.0000 | | VV | |
| 110 | 107.720 | 1487062 | 0.4947 | 71.435 | 0.4668 | 0.0000 | | VV | |
| 111 | 108.190 | 709049 | 0.2359 | 37.254 | 0.2434 | 0.0000 | | VV | |
| 112 | 108.493 | 818254 | 0.2722 | 38.627 | 0.2524 | 0.0000 | | VV | |
| 113 | 109.013 | 631416 | 0.2101 | 35.016 | 0.2288 | 0.0000 | | VV | |
| 114 | 109.507 | 1010362 | 0.3361 | 33.653 | 0.2199 | 0.0000 | | VV | |
| 115 | 109.900 | 446664 | 0.1486 | 27.863 | 0.1821 | 0.0000 | | VV | |
| 116 | 110.160 | 598899 | 0.1993 | 33.360 | 0.2180 | 0.0000 | | VV | |
| 117 | 110.493 | 840683 | 0.2797 | 57.202 | 0.3738 | 0.0000 | | VV | |
| 118 | 111.023 | 2135668 | 0.7105 | 103.717 | 0.6777 | 0.0000 | | VV | |
| 119 | 111.450 | 547756 | 0.1822 | 42.198 | 0.2757 | 0.0000 | | VV | |
| 120 | 111.833 | 1597280 | 0.5314 | 56.890 | 0.3717 | 0.0000 | | VV | |
| 121 | 112.473 | 967994 | 0.3220 | 55.981 | 0.3658 | 0.0000 | | VV | |
| 122 | 112.607 | 679050 | 0.2259 | 59.614 | 0.3895 | 0.0000 | | VV | |
| 123 | 112.820 | 536941 | 0.1786 | 49.313 | 0.3261 | 0.0000 | | VV | |
| 124 | 113.067 | 987108 | 0.3284 | 35.926 | 0.2348 | 0.0000 | | VV | |
| 125 | 113.807 | 1383823 | 0.4604 | 34.665 | 0.2265 | 0.0000 | | VV | |
| 126 | 114.563 | 1002529 | 0.3335 | 36.357 | 0.2376 | 0.0000 | | VV | |
| 127 | 114.970 | 520199 | 0.1731 | 24.136 | 0.1577 | 0.0000 | | VV | |
| 128 | 115.540 | 1143580 | 0.3803 | 28.119 | 0.1837 | 0.0000 | | VV | |
| 129 | 116.577 | 338258 | 0.1125 | 11.209 | 0.0732 | 0.0000 | | VV | |
| 130 | 117.017 | 176187 | 0.0586 | 8.880 | 0.0580 | 0.0000 | | VV | |
| 131 | 117.400 | 169393 | 0.0564 | 8.586 | 0.0561 | 0.0000 | | VV | |
| 132 | 118.133 | 518740 | 0.1726 | 11.014 | 0.0720 | 0.0000 | | VV | |
| 133 | 118.763 | 134439 | 0.0447 | 7.091 | 0.0463 | 0.0000 | | VV | |
| 134 | 119.237 | 368278 | 0.1225 | 10.127 | 0.0662 | 0.0000 | | VP | |
| 135 | 121.140 | 64584 | 0.0215 | 2.560 | 0.0167 | 0.0000 | | PV | |
| 136 | 121.620 | 185059 | 0.0616 | 6.282 | 0.0410 | 0.0000 | | VV | |
| 137 | 122.620 | 30314 | 0.0101 | 1.935 | 0.0126 | 0.0000 | | VV | |
| 138 | 123.090 | 254238 | 0.0846 | 8.468 | 0.0553 | 0.0000 | | VV | |
| 139 | 124.110 | 141072 | 0.0469 | 6.206 | 0.0406 | 0.0000 | | VP | |

TABLE 1-continued

| No. | retention time | area (uv*sec) | area % | relative height | height % | conc | conc unit | basline | ingredient name |
|---|---|---|---|---|---|---|---|---|---|
| 140 | 125.877 | 378418 | 0.1259 | 7.976 | 0.0521 | 0.0000 | | | PP |
| 141 | 127.977 | 27554 | 0.0092 | 1.016 | 0.0066 | 0.0000 | | | PP |
| 142 | 129.813 | 187915 | 0.0625 | 9.937 | 0.0649 | 0.0000 | | | PP |
| | total | 300574826 | | 15303.60 | | 0.0000 | | | |

The differences between the invention's Zang Zhi fruiting body, other cultural methods and liquid cultural method were compared by the analysis of HPLC. The HPLC spectra-are shown in FIGS. 1(a)–(c); and the measurements are shown in Table 2 and Table 3. These spectra show that the inventions's Zang Zhi fruiting body and wild Zang Zhi have the same shape of peak, and also show that the invention's cultured Zzang Zhi fruiting body and that of wild ZangZhi have the same activities and functions.

Table 2. HPLC Spectrum Figure of Liquid Cultured Zang Zhi

TABLE 2

| No. | retention time | area (uv*sec) | area % | relative height | height % | conc | conc unit | basline | ingredient name |
|---|---|---|---|---|---|---|---|---|---|
| 1 | 1.620 | 262998 | 1.2184 | 33.745 | 2.2045 | 0.0000 | | | PV |
| 2 | 1.357 | 8294342 | 38.4242 | 660.685 | 37.5912 | 0.0000 | | | VV |
| 3 | 2.520 | 5417475 | 25.0969 | 726.398 | 41.3301 | 0.0000 | | | VV |
| 4 | 2.820 | 1692534 | 7.8413 | 99.406 | 5.6559 | 0.0000 | | | VV |
| 5 | 3.790 | 731157 | 3.3871 | 23.209 | 1.3205 | 0.0000 | | | VB |
| 6 | 4.123 | 271974 | 1.2599 | 11.713 | 0.6664 | 0.0000 | | | BV |
| 7 | 4.623 | 164068 | 0.7137 | 7.810 | 0.4444 | 0.0000 | | | VV |
| 8 | 5.023 | 154230 | 0.7145 | 4.580 | 0.2606 | 0.0000 | | | VV |
| 9 | 5.897 | 29822 | 0.1382 | 1.652 | 0.0940 | 0.0000 | | | VP |
| 10 | 7.860 | 150572 | 0.6975 | 5.210 | 0.2964 | 0.0000 | | | PP |
| 11 | 9.210 | 123419 | 0.5717 | 3.914 | 0.2227 | 0.0000 | | | PP |
| 12 | 11.930 | 130807 | 0.6060 | 3.563 | 0.2027 | 0.0000 | | | PV |
| 13 | 12.740 | 37712 | 0.1747 | 1.232 | 0.0701 | 0.0000 | | | VP |
| 14 | 15.103 | 504463 | 2.3370 | 11.048 | 0.6286 | 0.0000 | | | PP |
| 15 | 16.890 | 143477 | 0.6647 | 3.512 | 0.1998 | 0.0000 | | | PP |
| 16 | 19.350 | 56860 | 0.2634 | 1.827 | 0.1039 | 0.0000 | | | PP |
| 17 | 23.510 | 806878 | 3.7379 | 11.274 | 0.6415 | 0.0000 | | | PP |
| 18 | 27.167 | 92042 | 0.4264 | 1.224 | 0.0696 | 0.0000 | | | PP |
| 19 | 30.633 | 144285 | 0.6684 | 2.243 | 0.1276 | 0.0000 | | | PP |
| 20 | 33.747 | 239568 | 1.3414 | 3.947 | 0.2245 | 0.0000 | | | PP |
| 21 | 38.727 | 250488 | 1.1604 | 3.231 | 0.1839 | 0.0000 | | | PP |
| 22 | 41.340 | 61644 | 0.2856 | 0.771 | 0.0438 | 0.0000 | | | PP |
| 23 | 43.727 | 29928 | 0.1386 | 0.470 | 0.0267 | 0.0000 | | | PP |
| 24 | 57.047 | 112074 | 0.5192 | 9.096 | 0.5175 | 0.0000 | | | PV |
| 25 | 57.433 | 175711 | 0.8140 | 10.275 | 0.5846 | 0.0000 | | | VV |
| 26 | 57.907 | 107598 | 0.4985 | 4.508 | 0.2565 | 0.0000 | | | VV |
| 27 | 58.137 | 25810 | 0.1196 | 2.279 | 0.1296 | 0.0000 | | | VP |
| 28 | 61.380 | 23245 | 0.1077 | 2.024 | 0.1152 | 0.0000 | | | PV |
| 29 | 62.743 | 196612 | 0.9108 | 21.767 | 1.2385 | 0.0000 | | | VV |
| 30 | 64.223 | 30411 | 0.1409 | 2.094 | 0.1192 | 0.0000 | | | PV |
| 31 | 64.717 | 441196 | 2.0439 | 41.620 | 2.3681 | 0.0000 | | | VV |
| 32 | 64.997 | 48524 | 0.2248 | 4.870 | 0.2771 | 0.0000 | | | VV |
| 33 | 65.420 | 40354 | 0.1869 | 3.529 | 0.2008 | 0.0000 | | | VV |
| 34 | 65.833 | 67766 | 0.3139 | 3.823 | 0.2175 | 0.0000 | | | VP |
| 35 | 66.950 | 21298 | 0.0987 | 1.691 | 0.0962 | 0.0000 | | | PP |
| 36 | 67.773 | 32193 | 0.1491 | 1.708 | 0.0972 | 0.0000 | | | PP |
| 37 | 79.013 | 29414 | 0.1363 | 0.920 | 0.0523 | 0.0000 | | | PP |
| 38 | 97.297 | 21884 | 0.1014 | 0.456 | 0.0260 | 0.0000 | | | PP |
| 39 | 100.053 | 38474 | 0.1782 | 0.738 | 0.0420 | 0.0000 | | | PP |
| 40 | 104.457 | 126686 | 0.5869 | 2.358 | 0.1342 | 0.0000 | | | PP |
| 41 | 107.010 | 57252 | 0.2652 | 2.113 | 0.1202 | 0.0000 | | | PP |
| 42 | 111.397 | 35854 | 0.1661 | 4.236 | 0.2410 | 0.0000 | | | VV |
| 43 | 111.813 | 28337 | 0.1313 | 2.512 | 0.1429 | 0.0000 | | | VP |
| 44 | 113.790 | 25408 | 0.1177 | 1.810 | 0.1030 | 0.0000 | | | VP |
| 45 | 115.883 | 43858 | 0.2032 | 3.808 | 0.2167 | 0.0000 | | | PV |
| 46 | 119.590 | 25451 | 0.1179 | 1.656 | 0.0942 | 0.0000 | | | PP |
| | total | 21586254 | | 1757.553 | | 0.0000 | | | |

Table 3. HPLC Spectrum Figure of Wild Zang Zhi

TABLE 3

| No. | retention time | area (uv*sec) | area % | relative height | height % | conc | conc unit | basline | ingredient name |
|---|---|---|---|---|---|---|---|---|---|
| 1 | 1.550 | 1332009 | 0.5787 | 162.045 | 1.1488 | 0.0000 | | PV | |
| 2 | 1.913 | 12708000 | 5.5210 | 797.430 | 5.6535 | 0.0000 | | VV | |
| 3 | 2.607 | 7990504 | 3.4715 | 374.149 | 2.6526 | 0.0000 | | VV | |
| 4 | 2.997 | 3336181 | 1.4494 | 151.464 | 1.0738 | 0.0000 | | VV | |
| 5 | 3.480 | 827969 | 0.3597 | 90.536 | 0.6419 | 0.0000 | | VV | |
| 6 | 3.687 | 2100942 | 0.9127 | 89.231 | 0.6326 | 0.0000 | | VV | |
| 7 | 4.110 | 1665378 | 0.7235 | 80.468 | 0.5705 | 0.0000 | | VV | |
| 8 | 4.590 | 986857 | 0.4287 | 61.543 | 0.4363 | 0.0000 | | VV | |
| 9 | 4.867 | 1300649 | 0.5651 | 59.445 | 0.4214 | 0.0000 | | VV | |
| 10 | 5.377 | 620409 | 0.2695 | 37.086 | 0.2629 | 0.0000 | | VV | |
| 11 | 5.623 | 712514 | 0.3095 | 37.666 | 0.2670 | 0.0000 | | VV | |
| 12 | 6.020 | 617412 | 0.2682 | 32.787 | 0.2324 | 0.0000 | | VV | |
| 13 | 6.347 | 380678 | 0.1654 | 24.939 | 0.1768 | 0.0000 | | VV | |
| 14 | 6.660 | 622333 | 0.2704 | 24.053 | 0.1705 | 0.0000 | | VV | |
| 15 | 7.060 | 557302 | 0.2421 | 18.364 | 0.1302 | 0.0000 | | VV | |
| 16 | 7.710 | 585765 | 0.2545 | 27.106 | 0.1922 | 0.0000 | | VV | |
| 17 | 8.353 | 276221 | 0.1200 | 10.957 | 0.0777 | 0.0000 | | VV | |
| 18 | 8.867 | 379887 | 0.1650 | 19.904 | 0.1411 | 0.0000 | | VV | |
| 19 | 9.327 | 316284 | 0.1374 | 21.157 | 0.1500 | 0.0000 | | VV | |
| 20 | 9.623 | 72843 | 0.0316 | 4.914 | 0.0348 | 0.0000 | | VV | |
| 21 | 10.593 | 120581 | 0.0524 | 6.584 | 0.0457 | 0.0000 | | PP | |
| 22 | 11.260 | 57846 | 0.0251 | 2.283 | 0.0162 | 0.0000 | | PV | |
| 23 | 11.747 | 32476 | 0.0141 | 2.199 | 0.0156 | 0.0000 | | VV | |
| 24 | 12.253 | 209326 | 0.0909 | 11.437 | 0.0811 | 0.0000 | | VV | |
| 25 | 12.837 | 131315 | 0.0570 | 6.603 | 0.0468 | 0.0000 | | VV | |
| 26 | 13.733 | 270732 | 0.1176 | 7.438 | 0.0527 | 0.0000 | | VP | |
| 27 | 15.300 | 156380 | 0.0679 | 6.542 | 0.0464 | 0.0000 | | PP | |
| 28 | 17.513 | 346774 | 0.1507 | 10.369 | 0.0735 | 0.0000 | | PV | |
| 29 | 18.270 | 1011777 | 0.4396 | 25.904 | 0.1837 | 0.0000 | | VV | |
| 30 | 19.863 | 298337 | 0.1296 | 7.175 | 0.0509 | 0.0000 | | VP | |
| 31 | 21.567 | 237547 | 0.1032 | 6.715 | 0.0476 | 0.0000 | | VV | |
| 32 | 22.657 | 261555 | 0.1136 | 7.129 | 0.0505 | 0.0000 | | VV | |
| 33 | 23.960 | 419821 | 0.1824 | 8.165 | 0.0579 | 0.0000 | | VP | |
| 34 | 26.780 | 1014237 | 0.4405 | 20.361 | 0.1444 | 0.0000 | | PP | |
| 35 | 29.320 | 4482109 | 1.9472 | 103.960 | 0.7370 | 0.0000 | | PP | |
| 36 | 32.017 | 6999710 | 3.0410 | 156.204 | 1.1074 | 0.0000 | | PV | |
| 37 | 33.343 | 399151 | 0.1734 | 8.733 | 0.0619 | 0.0000 | | VP | |
| 38 | 35.053 | 97125 | 0.0422 | 2.428 | 0.0172 | 0.0000 | | PV | |
| 39 | 37.007 | 3062612 | 1.3305 | 46.150 | 0.3272 | 0.0000 | | VP | |
| 40 | 39.587 | 832484 | 0.3617 | 15.926 | 0.1129 | 0.0000 | | PV | |
| 41 | 40.897 | 2411303 | 1.0476 | 30.354 | 0.2152 | 0.0000 | | VP | |
| 42 | 43.603 | 94412 | 0.0410 | 2.102 | 0.0149 | 0.0000 | | PP | |
| 43 | 46.093 | 950329 | 0.4129 | 12.948 | 0.0918 | 0.0000 | | PP | |
| 44 | 47.820 | 29686 | 0.0129 | 0.697 | 0.0049 | 0.0000 | | PP | |
| 45 | 51.273 | 22016 | 0.0096 | 0.505 | 0.0036 | 0.0000 | | PP | |
| 46 | 53.253 | 391511 | 0.1701 | 6.542 | 0.0464 | 0.0000 | | PP | |
| 47 | 55.177 | 418679 | 0.1819 | 6.082 | 0.0431 | 0.0000 | | PP | |
| 48 | 57.243 | 3988680 | 1.7329 | 240.883 | 1.7078 | 0.0000 | | PV | |
| 49 | 57.500 | 4155318 | 1.8053 | 345.611 | 2.4503 | 0.0000 | | VV | |
| 50 | 57.787 | 3545656 | 1.5404 | 257.829 | 1.8279 | 0.0000 | | VV | |
| 51 | 58.010 | 1206951 | 0.5244 | 175.620 | 1.2451 | 0.0000 | | VV | |
| 52 | 58.257 | 2986313 | 1.2974 | 222.955 | 1.5807 | 0.0000 | | VV | |
| 53 | 58.400 | 5093407 | 2.2128 | 431.601 | 3.0599 | 0.0000 | | VV | |
| 54 | 58.673 | 2540255 | 1.1036 | 286.541 | 2.0315 | 0.0000 | | VV | |
| 55 | 58.943 | 5661787 | 2.4597 | 471.025 | 3.3394 | 0.0000 | | VV | |
| 56 | 59.233 | 2400643 | 1.0430 | 197.347 | 1.3991 | 0.0000 | | VV | |
| 57 | 59.543 | 3531683 | 1.5343 | 200.445 | 1.4211 | 0.0000 | | VV | |
| 58 | 59.850 | 2228945 | 0.9684 | 164.165 | 1.1639 | 0.0000 | | VV | |
| 59 | 60.060 | 2828869 | 1.2290 | 335.781 | 2.3806 | 0.0000 | | VV | |
| 60 | 60.410 | 17547630 | 7.6235 | 994.818 | 7.0529 | 0.0000 | | VV | |
| 61 | 60.743 | 13833800 | 6.0101 | 994.628 | 7.0516 | 0.0000 | | VV | |
| 62 | 60.920 | 9930270 | 4.3142 | 941.167 | 6.6726 | 0.0000 | | VV | |
| 63 | 61.343 | 3601150 | 1.5645 | 265.761 | 1.8842 | 0.0000 | | VV | |
| 64 | 61.723 | 6048523 | 2.6278 | 525.238 | 3.7238 | 0.0000 | | VV | |
| 65 | 62.127 | 2249845 | 0.9774 | 160.527 | 1.1381 | 0.0000 | | VV | |
| 66 | 62.357 | 2349680 | 1.2380 | 152.131 | 1.0786 | 0.0000 | | VV | |
| 67 | 63.207 | 11335680 | 4.9248 | 886.220 | 6.2830 | 0.0000 | | VV | |
| 68 | 63.460 | 3758168 | 1.6327 | 214.761 | 1.5226 | 0.0000 | | VV | |
| 69 | 64.087 | 17403430 | 7.5609 | 992.676 | 7.0377 | 0.0000 | | VV | |
| 70 | 64.807 | 6379895 | 2.7717 | 332.965 | 2.3606 | 0.0000 | | VV | |
| 71 | 65.487 | 1105522 | 0.4803 | 48.756 | 0.3457 | 0.0000 | | VV | |
| 72 | 66.060 | 1061718 | 0.4613 | 41.562 | 0.2947 | 0.0000 | | VV | |
| 73 | 66.490 | 1903467 | 0.8270 | 65.469 | 0.4642 | 0.0000 | | VV | |
| 74 | 67.563 | 1016818 | 0.4418 | 30.915 | 0.2192 | 0.0000 | | VV | |

TABLE 3-continued

| No. | retention time | area (uv*sec) | area % | relative height | height % | conc | conc unit | basline | ingredient name |
|---|---|---|---|---|---|---|---|---|---|
| 75 | 68.387 | 1511594 | 0.6567 | 37.104 | 0.2631 | 0.0000 | | | VV |
| 76 | 69.390 | 10743430 | 4.6675 | 525.207 | 3.7306 | 0.0000 | | | VV |
| 77 | 70.583 | 358833 | 0.1559 | 13.087 | 0.0928 | 0.0000 | | | VV |
| 78 | 71.257 | 2732845 | 1.1873 | 127.212 | 0.9019 | 0.0000 | | | VV |
| 79 | 72.317 | 237862 | 0.1033 | 7.948 | 0.0563 | 0.0000 | | | VV |
| 80 | 72.730 | 245290 | 0.1066 | 6.784 | 0.0481 | 0.0000 | | | VV |
| 81 | 73.783 | 87523 | 0.0380 | 3.200 | 0.0227 | 0.0000 | | | VV |
| 82 | 74.250 | 127009 | 0.0552 | 4.136 | 0.0293 | 0.0000 | | | VV |
| 83 | 74.890 | 86115 | 0.0374 | 2.980 | 0.0211 | 0.0000 | | | VP |
| 84 | 76.973 | 28738 | 0.0125 | 1.165 | 0.0083 | 0.0000 | | | PP |
| 85 | 77.503 | 92275 | 0.0401 | 1.898 | 0.0135 | 0.0000 | | | PP |
| 86 | 80.060 | 508744 | 0.2210 | 11.408 | 0.0809 | 0.0000 | | | PP |
| 87 | 82.200 | 28158 | 0.0122 | 0.871 | 0.0062 | 0.0000 | | | PP |
| 88 | 84.293 | 79909 | 0.0347 | 1.534 | 0.0109 | 0.0000 | | | PP |
| 89 | 87.500 | 1092447 | 0.4746 | 24.011 | 0.1702 | 0.0000 | | | PV |
| 90 | 87.630 | 300046 | 0.1304 | 24.553 | 0.1741 | 0.0000 | | | VV |
| 91 | 87.893 | 332295 | 0.1661 | 25.603 | 0.1815 | 0.0000 | | | VV |
| 92 | 88.107 | 224523 | 0.0975 | 21.631 | 0.1534 | 0.0000 | | | VV |
| 93 | 88.397 | 717983 | 0.3119 | 37.094 | 0.2630 | 0.0000 | | | VV |
| 94 | 89.010 | 518852 | 0.2254 | 22.242 | 0.1577 | 0.0000 | | | VV |
| 95 | 89.237 | 307090 | 0.1334 | 21.551 | 0.1528 | 0.0000 | | | VV |
| 96 | 89.473 | 302635 | 0.1315 | 19.158 | 0.1358 | 0.0000 | | | VV |
| 97 | 90.007 | 4050733 | 1.7598 | 326.533 | 2.3150 | 0.0000 | | | VV |
| 98 | 91.020 | 376589 | 0.1636 | 16.743 | 0.1187 | 0.0000 | | | VV |
| 99 | 91.427 | 152969 | 0.0665 | 11.423 | 0.0810 | 0.0000 | | | VV |
| 100 | 91.643 | 205346 | 0.0892 | 11.033 | 0.0782 | 0.0000 | | | VV |
| 101 | 92.013 | 142333 | 0.0618 | 11.613 | 0.0823 | 0.0000 | | | VV |
| 102 | 92.157 | 268901 | 0.1158 | 11.479 | 0.0814 | 0.0000 | | | VV |
| 103 | 92.633 | 124915 | 0.0543 | 8.073 | 0.0572 | 0.0000 | | | VV |
| 104 | 93.083 | 908307 | 0.3946 | 88.376 | 0.6266 | 0.0000 | | | VV |
| 105 | 93.590 | 210904 | 0.0915 | 15.423 | 0.1093 | 0.0000 | | | VV |
| 106 | 94.063 | 323059 | 0.1404 | 22.173 | 0.1572 | 0.0000 | | | VV |
| 107 | 94.547 | 63428 | 0.0276 | 3.102 | 0.0220 | 0.0000 | | | VV |
| 108 | 95.123 | 29222 | 0.0127 | 2.059 | 0.0146 | 0.0000 | | | VP |
| 109 | 95.963 | 45135 | 0.0196 | 2.967 | 0.0210 | 0.0000 | | | VP |
| 110 | 98.950 | 58309 | 0.0253 | 3.644 | 0.0258 | 0.0000 | | | VP |
| 111 | 100.273 | 20525 | 0.0089 | 0.713 | 0.0051 | 0.0000 | | | PP |
| 112 | 105.563 | 38299 | 0.0166 | 1.804 | 0.0128 | 0.0000 | | | PP |
| 113 | 112.263 | 55710 | 0.0242 | 1.468 | 0.0104 | 0.0000 | | | PP |
| 114 | 126.417 | 44605 | 0.0194 | 0.861 | 0.0061 | 0.0000 | | | PP |
| | total | 230177556 | | 14105.03 | | 0.0000 | | | |

The following Analysis Examination and Pharmacology Examination demonstrate that according to the elements and functions of the concentrated product of the invention's cultured Zang Zhi fruiting body, its major elements include triterpenoid compounds, water-soluble polysaccharides and chitin.

Water Soluble Polysaccharides

Examination by the Food Analysis Center in Japan revealed that solid Zang Zhi fruiting body obtained by the invention's culture method contains a high volume of water soluble polysaccharides; each 100 g fruiting body having 1.2 to 6.5 g of water soluble polysaccharides.

Content of Heavy Metals

Atomic Spectrum Analysis made by the Mircoanalysis Laboratory of Atomic Science Department of National Ching Hwa University reveals the invention's solid-cultured Zang Zhi has a content of heavy metals as follows:

| | | |
|---|---|---|
| Na: 48.7 ppm | Mn: 10.9 ppm | Cd: ND |
| Mg: 767 ppm | Fe: 100 ppm | Cr: ND |
| Al: 41.6 ppm | Zn: 16.4 ppm | |
| Ca: 605 ppm | As: ND | |
| K: 0.560% | Hg: ND | |

Total Antioxidant Activity

A comparison among one gram of the concentrated powder of the invention's solid Zang Zhi substance, the powder of wild Zang Zhi, and the concentrated powder of Ganderma sp. reveals their equivalent of the number of micrograms of Vitamin C as follows:

| Source | Content of one gram powder/ equivalent to the number of micrograms of Vitamin C |
|---|---|
| Powder of wild Zang Zhi | 633 ug ascorbic acid/g |
| Concentrated Powder of Ganderma sp. | 854 ug ascorbic acid/g |
| Concentrated Powder of the invention's solid Zang Zhi substance | 1180 ug ascorbic acid/g |

The result shows that the total antioxidant activity of the invention's solid Zang Zhi substance is far higher than that of the fruiting body of wild Zang Zhi and that of Ganderma sp.

Toxicity Test

According to the experiment of the acute oral toxicity test LD50, the tested mice were each fed with 2,000 mg/kg of the solid powder of the invention's Zang Zhi, while the other mice were fed with the specially distilled water as control. The results show that the tested mice neither act abnormally nor die. Hence, the volume of the acute oral toxicity test LD50 is higher than 2000 mg/kg.

Ames Test

Under the Ames test, the invention's Zang Zhi is examined by the plate mixed assay. Five tested bacterial isolates are *Salmonella tiyphimurium* TA97, TA98, TA100, TA102 and TA1535. Each isolate is under five concentrations analysis of 312.5, 625, 1250, 2500 and 5000 ug/plate, respectively. Coincidentally, a negative control group and a positive control group specific to bacterial isolate are included, and each group is triplicate. Test results show that negative control group falls in the acceptable range, and positive control group reflects an increase of mutant bacterial colonies. Whether or not the bacterial isolates are treated under big mouse liver enzyme metabolic system (S9), all tested concentrates do not show an obvious increase of colonies of Ames tested isolates, as shown in table 4.

TABLE 4

*Salmonella typhimurium* Ames Test

| Test Target | Test examples | Feed dosage × Period | Test result |
|---|---|---|---|
| *Salmonella typhimurium* | Five mutant isolates required Histidine of TA97, TA98, TA100, TA102 and TA1535 | tested concentration (ug/plate) 312.5, 625, 1250, 2500 and 5000 plate mixed assay for triplicate. The assay was under constant temperature 37 ± 1° C. for 48–72 hours, and the mutant colonies calculated. | Whether under big mouse liver enzyme metabolic system (S9) or not, all tested concentrations show no significant increase of Ames test mutant colonies. Test result is negative. |

Anti-Lipid Peroxidation Ability Test

Figure 2:
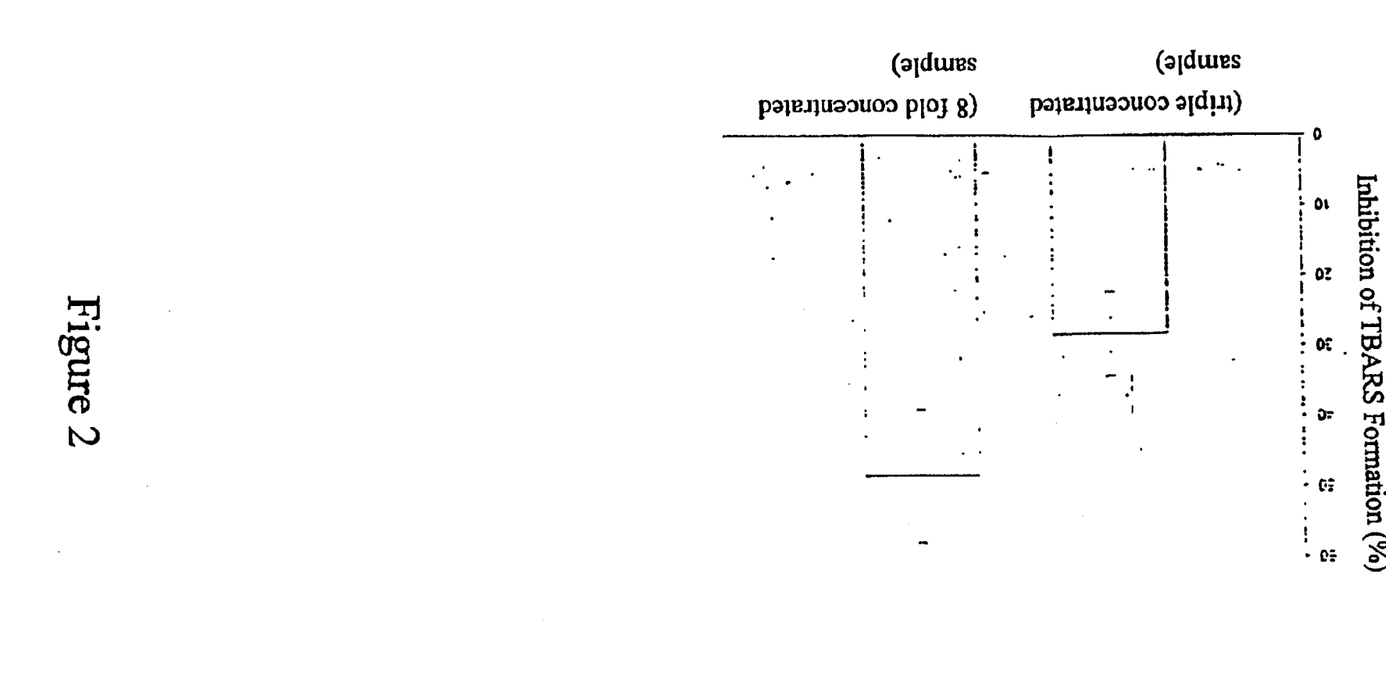
FIG. 2 illustrates the use of ferrous ions to stimulate the homogenization of mouse brain to cause the free radical peroxidative reaction of lipid, which will result in increasing of the TBARS (peroxidative constituents of lipid). Comparing the triple fold with the eight fold of concentrated extract of Zang Zhi fruiting body cultured according to the invention, we note that the increased inhibition of the peroxidative reaction will vary with the increase of the concentration, that is shown by the percentage of inhibition of per oxidative reaction (n=3).

Anti-lipid peroxidation ability and anti free radical ability of the solid cultured Zang Zhi solid concentrate was tested by the lipid peroxidation in mouse brain homogenization solution. Mouse brain homogenization solution exposed to an oxidative stress was stimulated by $Fe^{2+}$ introduction and induced the kinetics of generation of lipid-derived free radical. FIG. 2 shows that while increasing the concentration of triple and 8 fold the invention's Zang Zhi solid substance concentrate, it has a trend to inhibit lipid peroxidation and reduce the generation of free radical.

Protection of Liver Function Experiment

An experimental model using carbon tetrachloride to cause slow damage to the liver of a mouse to discover the effect of different concentrates of Zang Zhi on the slow damage to a mouse liver was established. Twenty-four mice (ICR strain) are divided into 4 groups as shown in Table 5.

TABLE 5

Zang Zhi Test Dosage and Animal Group Division

| Group | Carbon Tetrachloride Dosage | Dosage | No. of Mice |
|---|---|---|---|
| A | 0(control) | 0(control) | 6 |
| B | 40% $CCl_4$/olive oil (0.3 mg/100 g BW) | 0(control) | 6 |
| C | As above | 50 mg(triple)/Kg | 6 |
| D | As above | 50 mg(8 fold)/Kg | 6 |

Figure 3:
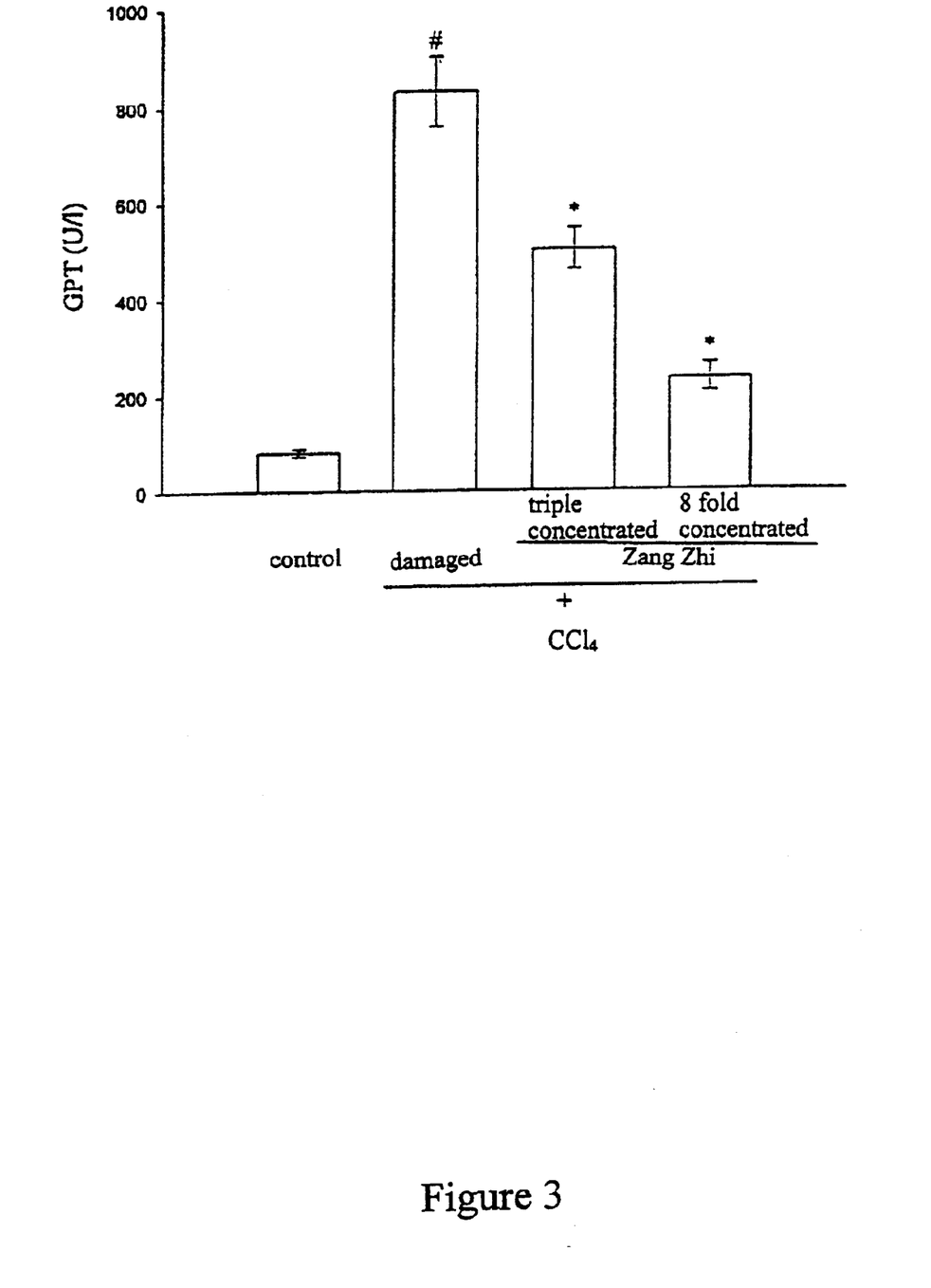
FIG. 3 shows the effect of different concentrations of extract of Zang Zhi on the active change of GTP for measurement of liver function. # represents the statistical difference between the normal group and the injury group (P<0.01); *represents the statistical difference between the feed group and the injury group (P<0.01). Value is represented by average±standard error.
Figure 4:
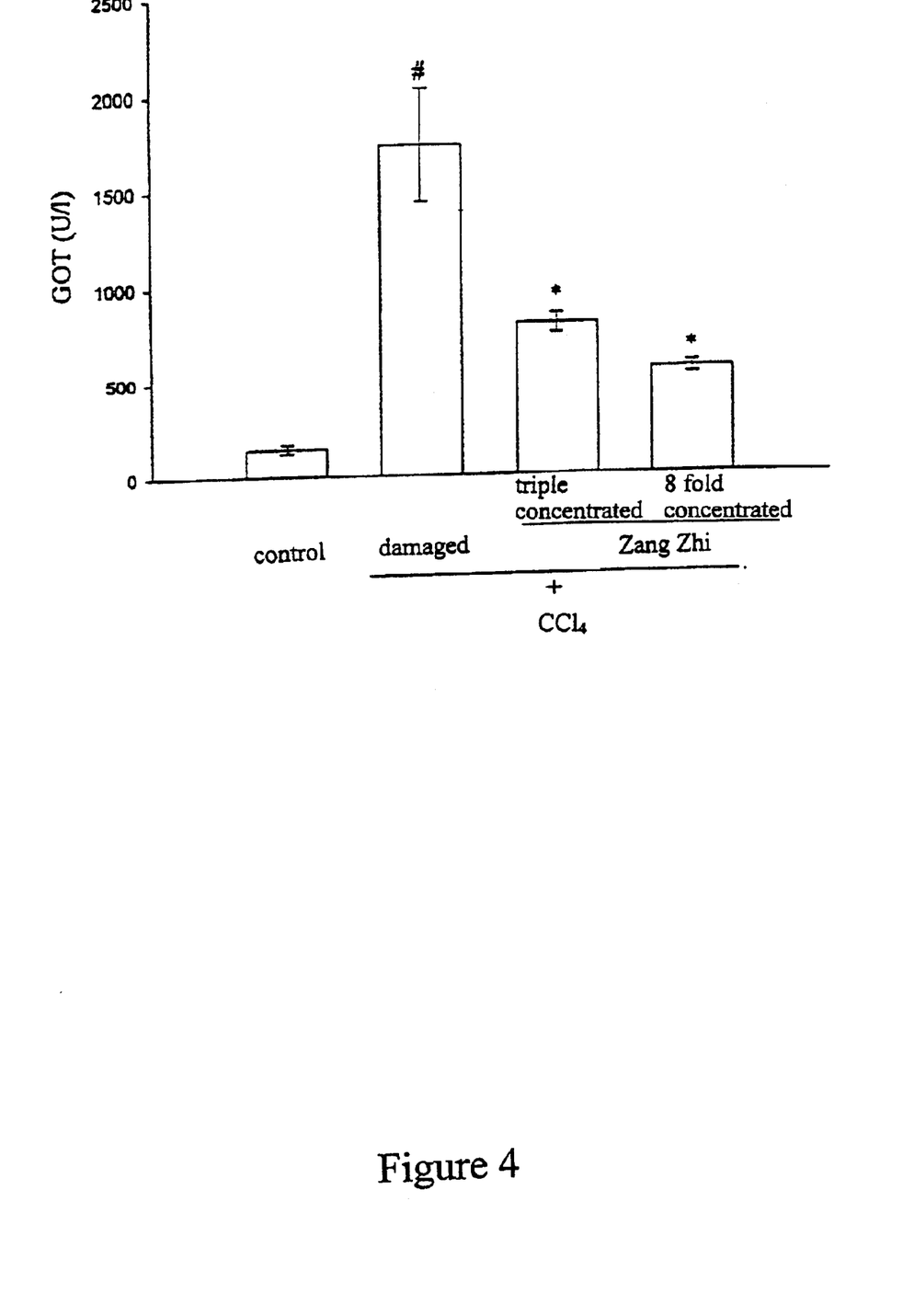
FIG. 4 shows the effect of different concentrations of Zang Zhi extract on the active change of GOT for the biochemical measurement of liver function. # represents the statistical difference between a normal group and an injury group (P<0.01); *represents the statistical difference between the feed group and the injury group (P<0.01). Value is represented by average±standard error.

The mice of Groups A and B to D were under a hypodermic injection of olive oil (0.1 ml/100 g BW), and 40% of $CCl_4$/Olive oil (0.3 ml/100 g BW) twice a week. The mice of Groups A and D were fed with physiological saline through a stomach tube, while the mice of Groups C and D were fed with two different dosages of extract of the invention's cultured Zang Zhi for five weeks. Then, the eyepit blood of all mice was collected to examine the biochemical measurement related to liver function. After that, the tested mice were sacrificed and the largest liver leaf was taken out to proceed with the hitopathogenic observation, such as damage to the liver cells, change of lipid, necrosis, cellulose and degree of these changes, and so on. Biochemical tests include activities of GTP and GOT, which are conducted according to the standards of International Clinic Chemistry. The experimental results show that GTP and GOT in the blood of a mouse liver damaged by carbon tetrachloride obviously increased after five weeks. GTP of about 850 units is 20–22 fold above the normal, and GOT of about 1700 units is 40–42 fold above the normal (FIGS. 3–4). In addition, mice fed with triple and eight fold of concentrated extract of the invention's Zang Zhi have the capacity to inhibit the increase of GTP and GOT induced by $CCl_4$. Particularly, when the GTP and GOT approach the peak, the triple concentrated extract can inhibit the increase of GTP by 37% and the increase of GOT by 65%.

When comparing the liver tissue of a normal mouse with the liver tissue of the mouse fed on $CCl_4$ after six weeks, the liver tissue treated with $CCl_4$ conspicuously shows tumefacient and gray rough surface. However, the liver tissue of the mouse fed on different concentrated Zang Zhi extracts shows no tumefacient and gray rough surface. Besides, by staining, one can see the pile of lipid granules, the tumid liver cells around the middle vein, macrophage and other irritated white blood cells infiltrating the liver cell space, and partial necrosis cells showing nodular transformation. However, the liver tissue of the mouse fed on different concentrated Zang Zhi extracts has no pathogenic changes as described above.

Table 6 shows the semi-quantification analysis of pathogenic mouse liver tissue. N represents the normal group, D represents $CCl_4$ damaged group, X3 represents the group fed on triple concentrated extract, X8 represents the group fed on eight fold concentrated extract. It is proved that the concentrated Zang Zhi extract can significantly improve the pathogenic changes.

TABLE 6

Semi-Quantification Analysis of Mouse Pathogenic Liver Tissue

|   | Inflammation of liver | Fat degeneration | Cell necrosis | | Tuberous transformation | Biliary Proliferation | Calcification |
|---|---|---|---|---|---|---|---|
|   |   |   | Local necrosis | Cosecutive necrosis |   |   |   |
| N | 0 | 0 | 0–1 | 0 | 0 | 0 | 0 |
| D | 2–3 | 2–3 | 2 | 2 | 0–1 | 1 | 0–1 |
| X3 | 1 | 1–2 | 0–1 | 1–2 | 0–1 | 0–1 | 0–1 |
| X8 | 0–1 | 0–1 | 0–1 | 1 | 0 | 0–1 | 0–1 |

Cancer Cells Inhibition Experiment

The Food Industry Research and Development Institute is entrusted to conduct an experiment to find out how the Zang Zhi solid cultured concentrate of this invention can inhibit cell growth of cervix cancer (HeLa), stomach cancer (AGS), breast cancer (MCF-7), liver cancer (HepG2), bowel cancer (COLO 320 HSR), etc. The results of cell growth inhibition are shown in Table 7. The Zang Zhi solid cultured concentrate of this invention can significantly inhibit the growth of tumor cells (up to 75% to 87%), especially the cells of breast cancer.

TABLE 7

Results of Cancer Cell Inhibition by Extract of Solid Cultured Zang Zhi

|   | Rate of Cell Growth Inhibition (%) | | |
|---|---|---|---|
| Cancer Cell Lines | Average (%) | ± | SD |
| Hela | 83 | ± | 3.1 |
| AGS | 84 | ± | 2.7 |
| HepG2 | 75 | ± | 2.4 |
| MCF-7 | 87 | ± | 1.4 |

*The final concentration of the tested sample is 10% of the original concentration.

Figure 5:
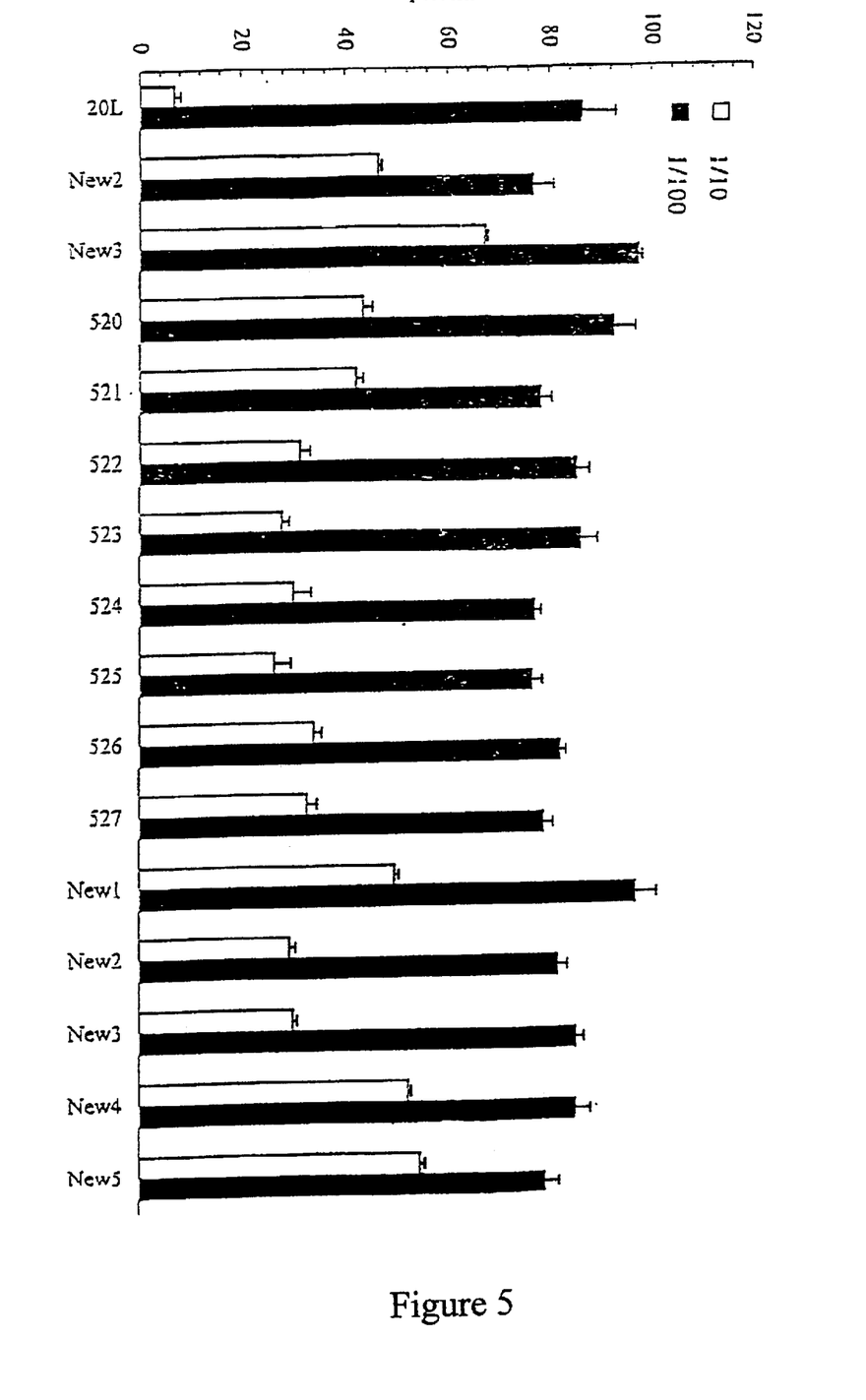
FIG. 5 shows the effect of an extract of Zang Zhi powder on the growth of bowel cancer cell (COLO 320 HSR).

In addition, an experiment is conducted to find out the results of inhibiting bowel cancer growth by using 5 powder specimens (New1, New2, New3, New4 and New5), 11 liquid specimens (20L, New2, New3, 520, 521, 522, 523, 524, 525, 526 and 527) as well as their 1:10 specimen dilution by microculture tetrazolium assay. The results as shown in FIG. 5 reveal that in the final concentration $\frac{1}{10}$ of stock solution can at least inhibit 30% of cancer cell growth, and the specimen 20L can inhibit the growth of cancer cells up to 90%.

Analysis of Chromosome Mutation in Vitro

Further, an analysis of chromosome configuration mutation in vitro was conducted to treat Chinese hamster ovary cells with the invention's Zang Zhi. The cells at middle mitosis were analyzed to observe and measure the frequency of abnormal chromosomes. Analysis of the configuration mutation of chromosome can estimate the ability of the invention's Zang Zhi to damage the cellular chromosome. Three treatments are given as follows: the first treatment is to add the invention's Zang Zhi to treat the cells for three hours, without adding the active mouse liver enzymes system (S9); the second one is to add S9 to treat the cells for 3 hours; and the third one is to treat the cells without adding S9 for 20 hours. All tested Zang Zhi concentrations under these three treatments cause no increase of the frequency of chromosomal configuration mutation. The experimental results are shown in the following Table 8.

TABLE 8

Analysis of Chromosomal Configuration Mutation

| Experimental Target | Experimental Examples | Feed Period | Result |
|---|---|---|---|
| Chinese hamster ovary cells; ATCC, repository No. CCL-61 CHO-KI | Inoculate each 60 mm cell cultured plate according to the tested concentrations; each concentration has two plates; these samples are divided into three groups according to the different treatments. | The tested concentrations of the first and second groups are 0, 312.5 625, 1250, 2500 and 5000 ug/ml. The tested concentrations of the third groups are 0, 30, 100, 1000, and 3000 ug/ml. After culture under different conditions, cells with scattered uniformly 18–21 chromosomes are selected for observation. | Results of the third group under treatment reveal that treatment of Chinese hamster ovary cells with the invention's Zang Zhi, before or after metabolic activities, does not show significant increase of the frequency of chromosomal configuration mutation of Chinese hamster ovary cells. The experimental result is negative. |

Analysis of Micronuclei in Animal Body

The clastogenicity of the invention's Zang Zhi in the animal body was examined. Further, the risk estimation of human hereditary toxicity was made according to the formation of micronuclei in reticular mouse red blood cells. Twenty-five mice were divided into 5 groups in this experiment. Analysis of the micronuclei reveals that the reaction of invention's Zang Zhi to circumference blood micronuclei of mouse is negative.

TABLE 9

Analysis of Micronuclei in Animal Body

| Experimental Target | Experimental Samples | Feed period | Experimental Results |
|---|---|---|---|
| ICR mouse | Samples are: 1. Solvent control group 2. High dosage control group 3. Medium dosage control group 4. Low dosage control group 5. Positive control group 6. Each group has five mice. | $1^{st}$–$4^{th}$ groups of mice respectively were fed on 0, 500, 1000, 2000 mg/Kg dosage; Mice of positive control group were fed on 1.0 mg/Kg MMC. The blood was collected and the reticular red blood cells were observed under fluorescent microscopy. | 1. There is no difference between tested dosage group and solvent control group. 2. The rate of reticular red blood cell analysis proves that high dosage would not be toxic to mouse marrow. 3. There is no tendency of dosage reaction to micronuclei rate and the comparison of the control group shows no significant increase. Thus analysis of the reaction of micronuclei of mouse circumference blood to Zang Zhi shows negative reaction. |

According to the pharmacological data described above, the invention's solid Zang Zhi substance not only possesses active constituents similar to wild Zang Zhi, for example, polysaccharide and tertripoid, but also possess the same function of anti-lipid peroxidation, anti-free radicals and anti-oxidation. Besides, the invention's solid Zang Zhi substance possesses the function to protect the liver and fight against cancer.

While this invention has been described in detail with particular reference to its preferred embodiments, the principles and modes of operation of the invention have also been described in this specification. The invention should not be construed as being limited to the particular forms disclosed, which are illustrative rather than restrictive. Modifications, variations, and changes may be made by those skilled in the art without departure from the spirit and scope of the invention as described by the following claims.

What is claimed is:

1. A cultured fungus product of *Antrodia camphorata* prepared by a process comprising:
    (a) culturing spawn of a wild-type fungus of *Antrodia camphorata* in a bag containing a medium comprising 10–70% of a cellulolytic substance, 10–30% of a starch, 5–15% of millet, 1–10% of a saccharide, 0.5–2% of a phosphate and 0.1–1% of a sulfite salt at a relative humidity of 60–80%, the medium having a neutral pH, the culturing being carried out at a temperature of 5–32° C. in an atmosphere comprising 0.1–1% carbon dioxide;
    (b) removing the medium from the bag;
    (c) exposing the removed medium to air and maintaining the removed medium in the air for a period of days until a solid fruiting body is formed of conoid shape, said removed medium being maintained in the air at a temperature which differs between days and nights with the removed medium being maintained during the days at a temperature between 20° and 30° C. and during the nights at a temperature of 10–12° C., wherein the humidity of the air is between 90–95% and the air contains less than 1% of carbon dioxide; and
    (d) recovering the solid fruiting body of conoid shape.

2. The cultured fungus product of claim 1, wherein the removed medium in step (c) is maintained during the days at a temperature that is 15° C. higher than the temperature during the nights.

3. The cultured fungus product of claim 1 which has a high pressure liquid chromatography spectrum substantially as shown in FIG. 1(a) of the drawings.

4. The cultured fungus product of claim 1, wherein the recovered solid fruiting body of conoid shape is about 10–30 cm in diameter, 15–30 cm in height and 0.2–0.6 kg in weight.

* * * * *

UNITED STATES PATENT AND TRADEMARK OFFICE
CERTIFICATE OF CORRECTION

PATENT NO. : 6,740,517 B2
DATED : May 25, 2004
INVENTOR(S) : Ming-Huang Lan et al.

It is certified that error appears in the above-identified patent and that said Letters Patent is hereby corrected as shown below:

<u>Title page</u>,
Item [76], Inventors, "7F, No. 9, Lane 191, Sec. 2, Di-Hua St., Taipei (TW); Li-Yu Wu," should read -- Chang-Chou Lan, Chung-Liang Lan, Chung-Min Lan, all of --

Signed and Sealed this

Eighth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,740,517 B2  
DATED : May 25, 2004  
INVENTOR(S) : Ming-Huang Lan et al.

It is certified that error appears in the above-identified patent and that said Letters Patent is hereby corrected as shown below:

<u>Title page,</u>
Insert Item -- [73] Assignee: Ming-Huang Lan and Li-Yu Wu, Taipei, TW --.

Signed and Sealed this

Twenty-seventh Day of September, 2005

JON W. DUDAS
*Director of the United States Patent and Trademark Office*